United States Patent [19]

Guala

[11] Patent Number: 4,842,826
[45] Date of Patent: Jun. 27, 1989

[54] DISPOSABLE DEVICE FOR COLLECTING PHYSIOLOGICAL SAMPLES, IN PARTICULAR COPROLOGICAL SAMPLES

[75] Inventor: Piergiacomo Guala, Alessandria, Italy

[73] Assignee: STA.TE. S.p.A., Alessandria, Italy

[21] Appl. No.: 35,046

[22] Filed: Apr. 6, 1987

[30] Foreign Application Priority Data

Apr. 16, 1986 [IT] Italy .................. 21561/86[U]

[51] Int. Cl.⁴ .......................... B01L 3/00; B65B 39/00
[52] U.S. Cl. ........................ 422/102; 422/100;
  422/101; 422/58; 220/366; 220/367; 141/331;
  141/344; 141/374; 141/379
[58] Field of Search ............ 422/99, 100, 102, 101,
  422/58, 301; 220/366, 367; 141/374, 331, 344,
  364, 379

[56] References Cited

U.S. PATENT DOCUMENTS

| | | | |
|---|---|---|---|
| 3,739,821 | 6/1973 | Watkin et al. | 141/374 X |
| 3,813,223 | 5/1974 | Fleck | 422/102 |
| 3,819,045 | 6/1974 | Greenwald | 209/17 |
| 3,936,373 | 2/1976 | Studer | 209/17 |
| 3,957,653 | 5/1976 | Blecher | 220/23 X |
| 4,066,646 | 1/1978 | LeBlanc, Jr. et al. | 422/102 |
| 4,203,840 | 5/1980 | Stoeppler et al. | 422/101 X |
| 4,214,993 | 7/1980 | Forsythe, Jr. et al. | 422/101 X |
| 4,225,575 | 9/1980 | Piasio et al. | 422/58 X |
| 4,288,316 | 9/1981 | Hennessy | 422/101 X |
| 4,388,997 | 6/1983 | Grime | 220/367 X |
| 4,427,634 | 1/1984 | Truglio | 422/102 X |
| 4,454,235 | 6/1984 | Johnson | 422/100 X |
| 4,528,187 | 7/1985 | Truglio | 422/102 |
| 4,563,332 | 1/1986 | Mitchell et al. | 422/102 X |
| 4,678,559 | 7/1987 | Szabados | 422/101 X |
| 4,735,905 | 4/1988 | Parker | 422/102 X |
| 4,800,156 | 1/1989 | Yuhda | 435/7 |

Primary Examiner—Barry S. Richman
Assistant Examiner—Lynn M. Kummert
Attorney, Agent, or Firm—Arnold, White & Durkee

[57] ABSTRACT

A device for collecting physiological samples, in particular coprological samples, which affords improved sanitary conditions of operation, comprises a container, a cap for said container, a pick-up stick fastened to the cap, a passageway extending through said cap, and a stopper for hermetically sealing off said passageway.

9 Claims, 1 Drawing Sheet

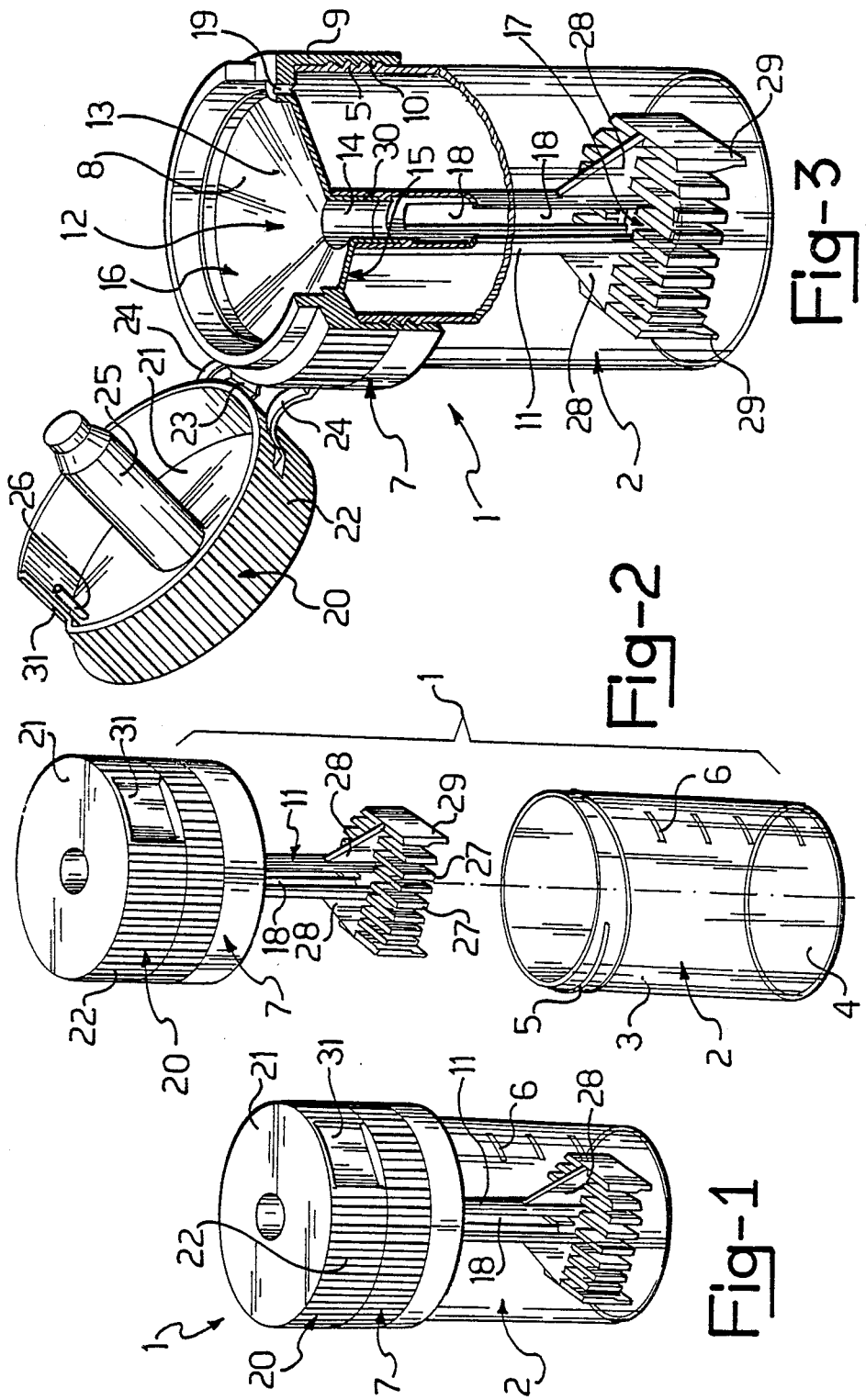

DISPOSABLE DEVICE FOR COLLECTING PHYSIOLOGICAL SAMPLES, IN PARTICULAR COPROLOGICAL SAMPLES

DESCRIPTION

This invention relates to a device for collecting physiological samples, and particularly coprological samples, of the type which includes a container, a cap for said container, and a pick-up stick fastened to the cap.

Such a device, while being in many ways advantageous and widely employed, still has a well-recognized drawback which becomes especially evident when a captured sample is to be tested in the laboratory.

It is in fact well known that, as a preliminary step, the sample should be dissolved in an appropriate liquid, to be poured in small amounts into the container. This is an extremely unpleasant operation to perform. First, the laboratory operator is likely to soil himself in manipulating the cap and container. Secondly, offensive odors are released by the sample.

It is an object of this invention to provide a device of the type specified hereinabove, which has such constructional and operational features as to obviate the above-mentioned drawbacks affecting similar prior art devices.

This object is achieved by a device comprising a passageway extending through said cap and a stopper for hermetically sealing said passageway.

Further features and the advantages of the device according to this invention will become apparent from the following detailed description of a preferred embodiment thereof, given by way of illustration and not of limitation with reference to the accompanying drawing, where:

FIG. 1 is a perspective view of a device according to the invention;

FIG. 2 is an exploded perspective view of the device of FIG. 1; and

FIG. 3 is a part-sectional enlarged scale view showing in perspective the device of FIG. 1 at a different stage of its operation.

Comprehensively designated 1 is a device for collecting generic physiological samples, and specifically, coprological samples.

The device 1 comprises a cylindrical container 2 having a cylindrical skirt 3 and bottom 4. It has an open top and is formed with an outside thread 5 at the upper edge portion of the cylindrical skirt 3.

The container 2 is formed as by a molding process from a suitable clear plastic, such as polystyrene. Marked along a generatrix line of the skirt 3 is a calibrated scale generally indicated at 6.

The device 1 further comprises a cap 7 which is mounted on the container 2 at the opening thereof. In particular, the cap 7 has a bottom 8 and a tubular portion 9 having a thread 10 formed on its inside. The cap 7 is threaded onto the container 2 by engaging the thread 10 with the thread 5.

Indicated at 11 is a pick-up stick, which is fastened to and extending downward from the bottom 8 of the cap 7 and extends toward the bottom 4 of the container 2.

The device 1 of this invention advantageously includes a passageway 12 of funnel-like shape, which comprises a first, conical section 13 extending axially through the bottom 8 of the cap 7, and a second, cylindrical section 14 extending axially through the pick-up stick 11. Thus, the bottom 8 and stick 11 jointly define a funnel 15 which has an inlet mouth 16 open upwards and an outlet mouth 17 open toward the bottom 4 of the container.

It should be noted that two opposing slots, both indicated at 18, are provided along the stick 11 which are cut in the second section 14 of the passageway 12. These slots 18 extend over a prevailing length along the stick 11.

In the cap 7, proximate to the tubular portion 9, there is provided a small diameter venting hole 19 which extends through the bottom 8.

The device 1 also comprises a stopper 20 effective to seal the passageway 12 tightly.

More specifically, the stopper 20 has a substantially cap-like configuration which includes a bottom 21 and a tubular portion 22. The stopper 20 is hinged to the cap 7 by means of a deformable bridge 23 which extends between the tubular portion 22 of the stopper 20 and the tubular portion 9 of the cap 7. The stopper 20 is displaceable angularly between a closed position, as shown in FIGS. 1 and 2, where the stopper 20 and cap 7 have their respective tubular portions, 9 and 22, arranged together, and an open position, as shown in FIG. 3, where the passageway 12 can be accessed from the outside. An overcenter intermediate position is provided between the open and closed positions. At that position, two ties 24, provided between the tubular portions 9 and 22 would be in a condition of maximum stretch.

A cylindrical tang 25, jutting out of the bottom 21 of the stopper 20 engages in the section 14 of the passageway 12, in tight-sealed male-to-female relationship, with the stopper 20 in the closed position.

Likewise, a cylindrical tang 26 jutting out of the bottom 21 of the stopper 20 engages in the vent hole 19 in tight-sealed male-to-female relationship.

In an advantageous way, the pick-up stick 11 has a working end for picking up a sample which is embodied by a plurality of reeds, collectively indicated at 27, which are disposed in a comb-like arrangement. The middle reeds in the plurality of reeds 27 jut directly out of the stick 11, whereas the end reeds are retained by radial ribs 28, in turn jutting out of the stick 11.

Each of the end reeds in the plurality of reeds 27 is advantageously provided with an extension 29 which extends toward the bottom 4 of the container 2 and is slightly tapered, thereby the reed is substantially spatulate.

The cap 7 and stopper 20 are molded integrally from a suitable plastic material having good mechanical properties and low-friction properties, such as an acetalic resin or nylon.

The pick-up stick 11 and reeds 27 are likewise formed as one piece, the pick-up stick 11 fitting snugly over a tubular lug 30 provided on the cap 7 at the bottom 8 thereof.

Thus, the stopper, cap, and pick-up stick form together a unit which can be handled as a whole.

A recess 31 is provided in the periphery of the stopper 20 to facilitate its opening, and an adhesive tamper-proof band, not shown in the drawing, would extend between the stopper 20, the cap 7 and the container 2.

The operation of the inventive device will be now described with reference to a starting condition, illustrated by FIG. 1, in which it is ready for use.

The cap 7 is first screwed off of the container 2, and by appropriate manipulation, the working end of the pick-up stick 11 is moved into engagement with the physiological sample to be picked up such that a portion of the sample is caught in the reeds 27.

Presently the cap is screwed back onto the container, and the device is transferred to the laboratory for testing the picked up sample.

The operator there will remove the stopper 20 and introduce into the container 2, through the funnel-like passageway 12, a set amount of a liquid diluent. In the meantime, air from the container interior is vented out through the vent hole 19. It should be noted that during that operation, some of the liquid diluent will flow directly into the container 2, to the bottom 4 thereof, and some will flow sideways out of the stick 11 through the slots 18, to sweep past the reeds 27 from above.

Thereafter, the sample thus diluted may be used as appropriate, and if required, applied to a slide by means of any of the spatulate reeds.

This device would be discarded after use.

The principal advantage afforded by the device of this invention resides in its improved sanitary performance. In fact, the liquid diluent can be brought into contact with a sample without involving any need for the operator to come into contact with the sample and virtually without releasing any offensive odors.

An additional advantage of the inventive device is that the picked up sample will be in nearly constant amounts, by virtue of the reed configuration of the working end of the pick-up stick.

Furthermore, it is virtually impossible to draw twice in sequence with the pick-up stick, thereby avoiding picking up an over-rich sample.

A further advantage of the device according to the invention is that it enables the spreading of an even layer of a sample over a slide by means of the spatulate reed.

Another advantage of the present invention is that it has a simple construction which can be readily produced in large volumes as dictated by a device of the disposable type.

Understandably, the device described hereinabove may be variously altered and modified by a skilled person in the art, as appropriate to meet specific contingent needs, without departing from the scope of the invention as set forth in the appended claims.

I claim:

1. A device for collecting physiological samples, in particular coprological samples, comprising a container, a cap for said container, and a pick-up stick fastened to and extending downward from a bottom of said cap toward a bottom of said container, said stick comprising at least one slot extending along a length thereof, a passageway extending through said cap and said pick-up stick and a stopper for hermetically sealing said passageway.

2. A device according to claim 1, wherein said passageway is funnel-like with a conical section extending through the cap and a cylindrical section extending through the pick-up stick.

3. A device according to claim 2, wherein a small vent hole extends through said cap.

4. A device according to claim 3, wherein a first, cylindrical tang extends from the stopper to hermetically seal off the cylindrical section of said passageway.

5. A device according to claim 4, wherein a second, cylindrical tang extends from the stopper to hermetically seal off the small vent hole.

6. A device according to claim 5, wherein the pick-up stick has a working end configured as a plurality of reeds disposed in a comb-like arrangement.

7. A device according to claim 6, wherein at least one end reed in said plurality of reeds is spatulate.

8. A device for collecting physiological samples comprising:
   a. a container;
   b. a cap mounted on top of said container, said cap comprising means defining a vent hole extending through a side thereof;
   c. a pick-up stick fastened to a bottom of said cap and having a working end extending therefrom;
   d. a passageway comprising a funnel-like section extending axially through said cap and further comprising a cylindrical section extending axially through said pick-up stick;
   e. a stopper for hermetically sealing said passageway;
   f. a first, cylindrical tang extending from said stopper to hermetically seal off the cylindrical section of said passageway;
   g. a second, cylindrical tang extending from said stopper to hermetically seal off said vent hole; and
   h. a plurality of reeds disposed in a comb-like arrangement affixed to the working end of said pick-up stick.

9. The device of claim 8 wherein said plurality of reeds contains at least one spatulate reed.

* * * * *